United States Patent
Struppler et al.

(10) Patent No.: US 6,652,443 B1
(45) Date of Patent: Nov. 25, 2003

(54) DEVICE FOR MAGNETICALLY STIMULATING A BODY PART

(76) Inventors: Albrecht Struppler, Maffeistrasse 6, Feldafing (DE); Peter Havel, Rappersdorf 2, Biburg (DE)

(*) Notice: Subject to any disclaimer, the term of this patent is extended or adjusted under 35 U.S.C. 154(b) by 0 days.

(21) Appl. No.: 09/701,888

(22) PCT Filed: Jun. 2, 1999

(86) PCT No.: PCT/EP99/03851

§ 371 (c)(1),
(2), (4) Date: Mar. 5, 2001

(87) PCT Pub. No.: WO99/62596

PCT Pub. Date: Dec. 9, 1999

(30) Foreign Application Priority Data

Jun. 2, 1998 (DE) ........................ 198 24 504

(51) Int. Cl.[7] .................................. A61N 2/02
(52) U.S. Cl. ........................................ 600/9
(58) Field of Search ................. 600/9, 13–14, 600/15; 607/48–49, 72, 62

(56) References Cited

U.S. PATENT DOCUMENTS

| | | | |
|---|---|---|---|
| 4,165,750 A | * 8/1979 | Aleev et al. ................. 607/48 |
| 4,428,366 A | * 1/1984 | Findl et al. .................. 600/14 |
| 4,492,233 A | * 1/1985 | Petrofsky et al. ............ 607/48 |
| 4,558,704 A | * 12/1985 | Petrofsky .................... 607/48 |
| 4,586,495 A | * 5/1986 | Petrofsky ..................... 602/2 |
| 4,669,477 A | * 6/1987 | Ober ........................... 607/48 |
| 4,838,272 A | 6/1989 | Lieber |
| 5,047,005 A | 9/1991 | Cadwell |
| 5,070,873 A | * 12/1991 | Graupe et al. ............... 607/48 |
| 5,133,354 A | * 7/1992 | Kallok ......................... 607/48 |
| 5,267,938 A | 12/1993 | Konotchick |
| 5,300,094 A | * 4/1994 | Kallok et al. ................ 607/42 |
| 5,562,707 A | * 10/1996 | Prochazka et al. ........... 607/2 |
| 5,620,463 A | 4/1997 | Drolet |
| 5,674,262 A | * 10/1997 | Tumey ......................... 607/48 |
| 5,718,662 A | 2/1998 | Jalinous |
| 5,725,471 A | 3/1998 | Davey et al. |
| 5,743,844 A | * 4/1998 | Tepper et al. ................ 600/14 |
| 5,759,198 A | * 6/1998 | Karell ......................... 607/48 |
| 5,984,854 A | * 11/1999 | Ishikawa et al. ............. 600/9 |
| 6,179,770 B1 | * 1/2001 | Mould ......................... 600/13 |
| 6,213,933 B1 | * 4/2001 | Lin ............................ 600/13 |
| 6,261,221 B1 | * 7/2001 | Tepper et al. ................ 600/14 |
| 6,282,448 B1 | * 8/2001 | Katz et al. ................... 607/48 |
| 2001/0018547 A1 | * 8/2001 | Mechlenburg et al. ........ 600/15 |

FOREIGN PATENT DOCUMENTS

WO 00/02624 * 1/2000

OTHER PUBLICATIONS

Bischoff, C. et al., "Magnetically Elicited Blind Reflex: An Alternative to Conventional Electrical Stimulation," Electromyography & Clinical Neurophysiology, Jul.–Aug. 1993, p. 265.*

* cited by examiner

*Primary Examiner*—John A. Jeffery
(74) *Attorney, Agent, or Firm*—Wood, Phillips, Katz, Clark & Mortimer

(57) ABSTRACT

The invention relates to a relates to a device for stimulating a body part. According to the invention, the device comprises at least two coils $S_i$ having at least one power supply for generating the magnetic fields at innervation zones of the body part, especially at end branchings of motor nerve fibers or peripheral nerves. The invention also relates to a device for controlling or regulating the at least one power supply provided for the coils $S_i$. The device for controlling or regulating the at least one power supply provided for the coils $S_i$ comprises at least one current pulse generator for emitting current pulses $I(S_i)$ with pulse frequencies $f(I(S_i))$ and pulse durations $d(I(S_i))$ by the at least one power supply provided for the coils $S_i$. The emission of the current pulses $I(S_i)$ causes the muscles of the body part to contract or relax in a coordinated manner so that a coordinated composed movement of the body part ensues.

20 Claims, 4 Drawing Sheets

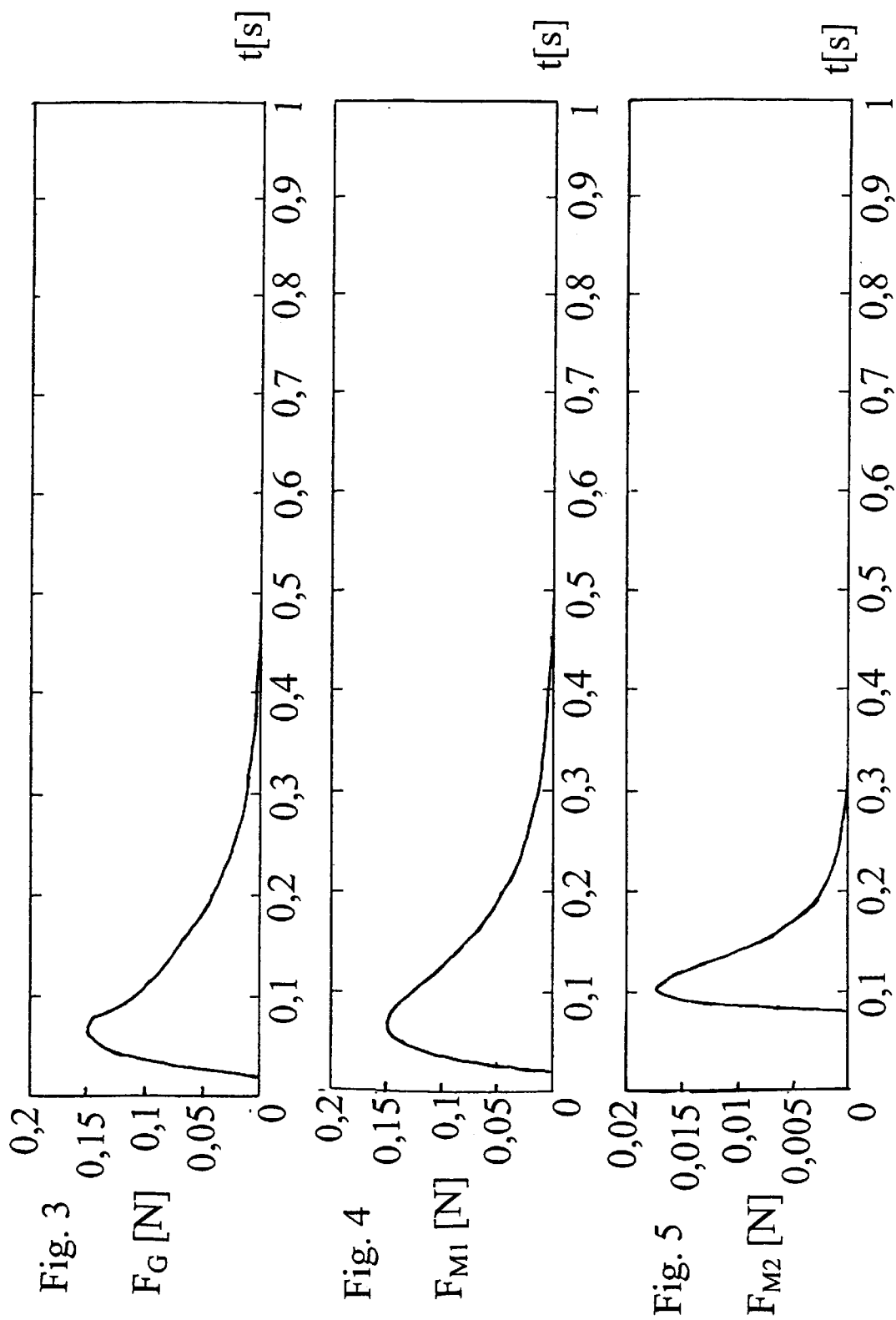

DEVICE FOR MAGNETICALLY STIMULATING A BODY PART

BACKGROUND OF THE INVENTION

The present invention relates to a device for the stimulation of a body part and to a method for the stimulation of a body part with the aid of an external stimulation device.

The treatment of centrally induced paralyses is one of the central problem areas in medical research. Central paralyses may occur on account of brain damage or spinal cord injuries. They are frequently caused by stroke syndromes, congenital brain damage, brain tumours or external injuries. Central paralyses are often accompanied by painful spastic muscle cramps. At present, they cannot be adequately cured by either surgery or medication.

Central paralyses can currently only be treated by conventional physiotherapy or by activating nerves or muscles of the paralysed body part by electric stimuli. For this purpose, electrodes are attached on or under the skin of the paralysed body part, so that an electric field is generated in the region of the nerves or muscles to be activated of the paralysed body part. This can only lead to a restricted reactivation of the muscles. Permanent rehabilitation, and consequently curing of the paralysis, cannot be achieved in this way however. What is more, considerable pain often occurs in this treatment.

U.S. Pat. No. 5,620,463 discloses an electrophysiological conditioning system which has conditioning applicators which transmit electromagnetic conditioning signals suitable for bringing about basic physiological effects, such as relaxation of the nervous system, stimulation of the blood circulation and stimulation of normal cell repair and regeneration, and are suitable for enhancing the natural self-defence and healing mechanisms of man and animals. For this purpose, magnetizing coils, which generate a magnetic field when a current pulse is discharged through the coil, are used. Such a conditioning system is not suitable, however, for the treatment of central paralyses.

The object of the present invention is to provide a method and a device for the treatment of central paralyses in such a way that a permanent rehabilitation effect is brought about.

The invention provides a device and a method for the stimulation of a paralysed body part, with the aid of which a smooth and pain-free composite and coordinated movement of the body part concerned can be induced. The failure of the proprioceptive afferences (biosensors, for example neuromuscular spindles) caused by the paralysis is to be replaced as far as possible to stimulate the plastic capabilities of the central nervous system as early as possible by a neuromodulation.

The device according to the invention for the stimulation of a body part has at least the following elements: at least two coils $S_i$ with at least one power supply for the generation of magnetic fields at innervation zones of the body part, particularly preferably at end branches of motor nerve fibres and peripheral nerves, and a device for the open-loop or closed-loop control of the power supply (supplies) for the coils. In this case, the device for the open-loop or closed-loop control of the power supply (supplies) for the coils has at least a current pulse generator for the emission of current pulses I ($S_i$) at pulse frequencies f (I($S_i$)) and pulse durations d (I($S_i$)) through the power supply (supplies) to the coils $S_i$, the emission of the current pulses taking place in such a way that the respective magnetic field pulses generate an electric field in the nerve paths, so that muscles of the body part are contracted or decontracted in a coordinated manner, so that a coordinated composite movement of the body part is obtained. This [lacuna] takes dependent factors into account, and an adaptation to neuronal erethisms takes place.

SUMMARY OF THE INVENTION

The device according to the invention consequently allows the generation of precisely defined movements of the centrally paralysed body part. These movements are often composed of a number of partial movements and simulate natural movements of the patient as faithfully as possible, for example grasping movements or walking movements. By a repetitive magnetic stimulation, primarily proprioceptive afferences are initiated both adequately by the induced movements and by direct activation of afferent nerve fibres. A regular repetition of induced movements can bring about a learning effect in the central nervous system, finally leading to the patient being able to perform the induced movements again independently (actively) with the paralysed body part. Starting from this partly rehabilitated state, the patient can then also re-learn other movements.

This method can basically be used for the treatment of any centrally paralysed body parts. It is not technically restricted to humans, but can also be used in the case of animals, for example racehorses, with local symptoms of paralysis.

The device according to the invention may have two or more coils $S_i$. Preferably three, four or five coils are used for the stimulation of the paralysed body part. For simple movements, a single coil may also be used. These coils must be of such a type that they can be positioned over innervation zones of the paralysed body part in such a way that an electric field is produced there by induction when a current pulse I ($S_i$) passes through the coil $S_i$.

Each coil $S_i$ preferably has a power supply, which generates the current pulses I ($S_i$) necessary for generating magnetic fields. However, a common power supply may also be used. These power supplies are controlled by a current pulse generator, which prescribes the point in time, frequency, duration and intensity of the current pulses I ($S_i$).

The current pulse generator generates the current pulses on the basis of prescribed patterns, which respectively correspond to certain composite sequences of movements, to be specific the physiological sequences of movements of the body part concerned. For this purpose, a multiplicity of patterns can be kept in a storage medium, which the current pulse generator can access at any time and which it can modify.

The intensity of the current pulses I ($S_i$) determines the field strength of the magnetic field respectively generated. The field strength of the magnetic field applied must exceed a certain threshold in order for a movement to be initiated. This threshold may vary with the body part concerned and with the patient.

The duration and frequency of the current pulses influence the performance of the induced movements, that is to say their roundness or angularity, to a considerable extent. However, the duration and frequency of the current pulses also have a great influence in the area of therapy. The pulse frequency f (I($S_i$)) preferably lies in a range from 10 Hz to 30 Hz, particularly preferably in a range from 15 Hz to 25 Hz. These frequencies lie in the physiological range for activating the muscles. A current pulse preferably corresponds here to a sinusoidal oscillation, on account of the optimization in terms of energy. The sinusoidal oscillation preferably has here, again with regard to its optimization in terms of energy, a period duration in a range from $1.9*10^{-4}$ s to $3.77*10^{-4}$ s, particularly preferably in a range from $1.19*10^{-4}$ s to $2.15*10^{-4}$ s. The segment extends preferably from 0 to a value in a range from 0 to $2\pi$, particularly preferably to a value of $k*\pi/4$, where k is 1, 2, 3 or 4. In a further preferred embodiment, the sinusoidal oscillation is broken off at a value in the range from 0 to $\pi/4$, so that a high value for dI $(S_i)$/dt is obtained, which brings with it an improved stimulation effect.

In a preferred embodiment, the device for the open-loop or closed-loop control of the power supply (supplies) for the coils $S_i$ has at least one sensor for sensing the momentary position of the body part, in order in this way to be able to control or regulate the power supply (supplies) for the coils correspondingly. Preferably, one or more, possibly also a combination, of the following sensors is used here: a position switch, preferably a 3-point switch, an angle potentiometer, an ultrasonic measuring system or an infrared camera. If angle-measuring potentiometers are used, an arrangement of three potentiometers, the angle signals of which are summated, is preferably chosen. As a result, the individual potentiometers do not have to be adapted exactly to the axis of the joint. In the case of an ultrasonic measuring system, ultrasonic transmitters are fastened at suitable points of the body part concerned. The signals of these transmitters are sensed by a fixed receiver with regard to their position. If infrared cameras are used, the position is calculated back from the image of two cameras by means of infrared LEDs fastened at suitable points of the corresponding body part.

In another preferred embodiment of the device, the device is specifically adapted to a particular patient, so that the device can also be used in a "feed-forward" mode without any sensors.

The device for the open-loop and closed-loop control of he power supply (supplies) for the coils preferably includes a closed-loop control unit which responds to a signal which represents at least one state parameter for at least one muscle of the body part. The state of a muscle comprises the mechanical expansion (elastic and damping factors) and the innervational, contractile muscle activation. This signal is preferably obtained from an electromyogram, which is measured at least one muscle of the body part. Electromyography represents a method of registering muscle action potentials. An electromyogram can consequently provide information on induced or voluntary, intended action potentials, by which the stimulated movement of the muscle concerned is supported. Consequently, not only the degree of paralysis and the rehabilitation already achieved but also the fatigue of the muscle can be determined. The influence of the support of the induced movements by the patient as a result of the patient's own willpower can also be quantitatively or qualitatively assessed with the aid of this method. This information makes it possible to adapt the current pulses I $(S_i)$, that is to say their intensity, frequency and duration, to the specific treatment situation of the patient. In this way, the rehabilitation can be individualized and intensified.

The closed-loop control of the treatment can in principle take place at any time intervals, for example after every few seconds, which would mean constant monitoring of the situation, or else after every few days or weeks, which would be equivalent to keeping a general watchful eye on the rehabilitation steps.

In a further preferred embodiment of the invention, the device for the open-loop or closed-loop control of the power supply (supplies) for the coils $S_i$ has at least one sensor for sensing forces acting on the corresponding body part, to make it possible in this way for the power supply (supplies) for the coils to be controlled or regulated in an adapted manner. This sensor is preferably a pressure-dependent resistor. For this purpose, a piezoelectric capacitance measurement is carried out, for example, or strain gauges are used.

Preferably, a learning ;algorithm is integrated in the device for the open-loop or closed-loop control of the power supply (supplies) for the coils. During a stimulation, the stimulation result and effect are observed, analysed and recorded in a memory unit. This allows the stimulation effect to be optimized patient-specifically in successive cycles. As an alternative to this, the procedure may also be such that the movement is initially performed under open-loop control, after completion of the movement the actual position of the body part is compared with its desired position and then the control parameters are changed in such a way that the aim is achieved even better when the next stimulation is carried out. This type of "feed-forward" control corresponds more closely to the physiological situation. This control can be realized for example by several neuro-controllers (neuronal networks) or by an adaptive control device. In a further possible way of using the learning algorithm, the stimulation pattern is adapted to the physiological generation of signals.

Further advantages, features and application possibilities for the invention emerge from the following description of an exemplary embodiment in conjunction with the drawing, in which:

BRIEF DESCRIPTION OF THE DRAWINGS

FIG. 3 shows a diagram of the variation over time of the force exerted by a muscle stimulated according to the invention, taking the secondary systems into account.

FIG. 4 shows a diagram of the variation over time of the force exerted by a muscle stimulated according to the invention, on the basis of the stimulation.

FIG. 5 shows a diagram of the variation over time of the force exerted by the antagonist.

DETAILED DESCRIPTION OF THE INVENTION

Figure 1:
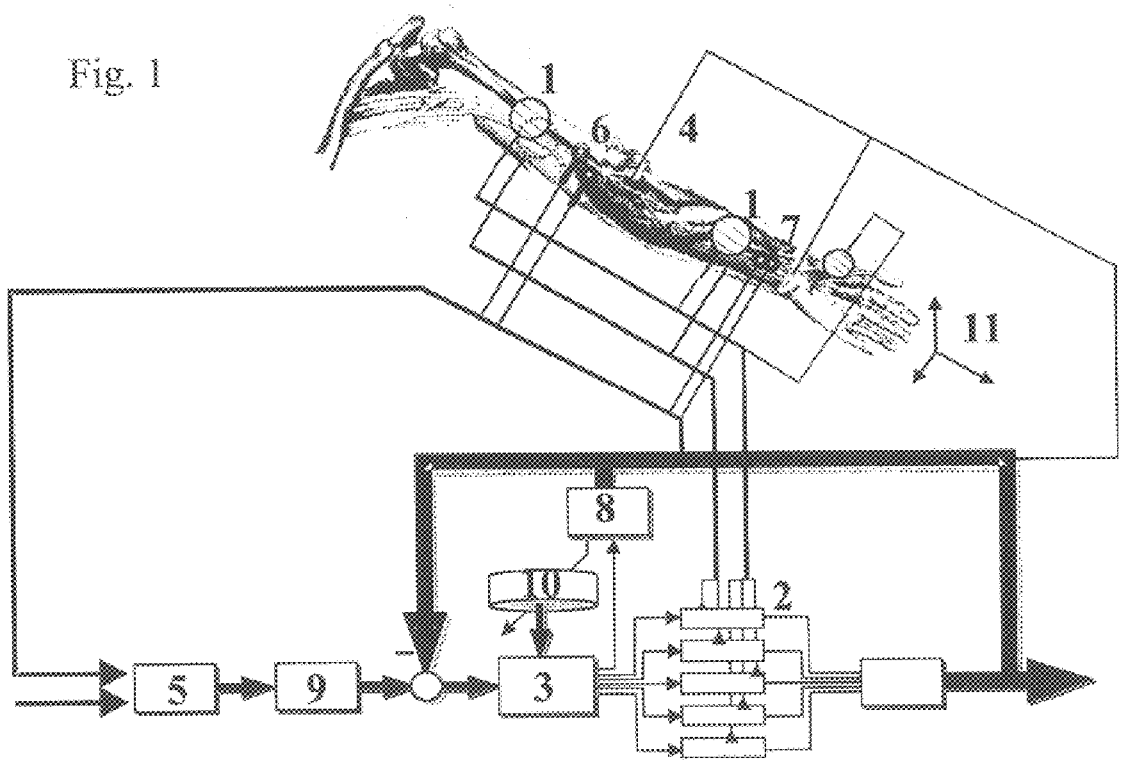
FIG. 1 shows a functional diagram of a device according to the invention, the body part to be stimulated being a human arm.

FIG. 1 represents a functional diagram of a device according to the invention. The device represented here serves for the stimulation or neurostimulation of a human arm. Five coils 1 are arranged on the arm in such a way that, in the state in which current is flowing through, they can generate magnetic fields at innervation zones of a corresponding muscle or a corresponding group of muscles of the arm. The five power supplies 2 for the five coils 1 are activated by means of a current pulse generator 3. The current pulse generator 3 is responsible for the generation of a corresponding current pulse pattern, which is necessary to achieve a stimulation of individual muscles or groups of muscles, which ultimately leads step by step to a certain selected movement of the arm, for example to bending of the arm. The stimulation of the muscles or groups of muscles must take place in this case in such a way that the muscles or groups of muscles are contracted or decontracted in a coordinated manner. Two coils 1 are in this case often not to be "operated", i.e. supplied with current, simultaneously, in order to prevent an unfavourable interaction of the corresponding magnetic fields, in particular to avoid a positive superimposing of the magnetic fields and accompanying enormous fields strengths.

Before a pulse pattern can be generated in the current pulse generator 3, a certain command is fed to the system by means of a closed-loop control unit 5. This may either be an external command for carrying out a specific movement or a voluntary activation (intention) of the patient concerned for a certain movement. The latter is measured by an electromyogram 6 of corresponding muscles. Once a command is received, this command is converted in a first step into system-intelligible individual commands by the closed-loop control unit 5. In a. further downstream closed-loop control unit 9, these individual commands are converted into movement segments with an associated movement- and force-tracing trajectory for the movement of the arm and the hand. A movement- and force-tracing trajectory comprises a plurality of transition points, each transition point comprising presettings for the angle of the joint and force on the fingers for the arm and hand. In the current pulse generator 3, a comparison between the desired position and the actual position is used as a basis for generating the current pulse patterns which respectively have to be emitted by the power supplies 2 for the coils 1 to the latter in order to stimulate the corresponding muscles or groups of muscles. For generating the pulse pattern, the current pulse generator 3 accesses a memory unit 10 which is integrated in the device and in which information specific to the body part or the patient is stored. With the aid of this information, consequently the current pulse pattern can be individually adapted and optimized. During a stimulation, the stimulation result and effect are observed and analysed by means of a learning algorithm 8, in order then to be optimized for the subsequent cycle.

The joint-angle positions and forces on the thumb and index finger are sensed and fed back by means of sensors 4, 7 and 11, for example angle potentiometers with pressure sensing via pressure-dependent resistors. The feedback serves for controlling the current pulses necessary for the subsequent movement step, which are to be emitted by the power supplies 2 to the coils 1. By measuring the forces on the thumb and index finger, a controlled grasping of objects or a force-controlled closing of the thumb and index finger for precision gripping is made possible.

This cycle is to be repeated until the prescribed movement has been completed, which is likewise established and reported by the sensors 4 and 7.

Figure 2:
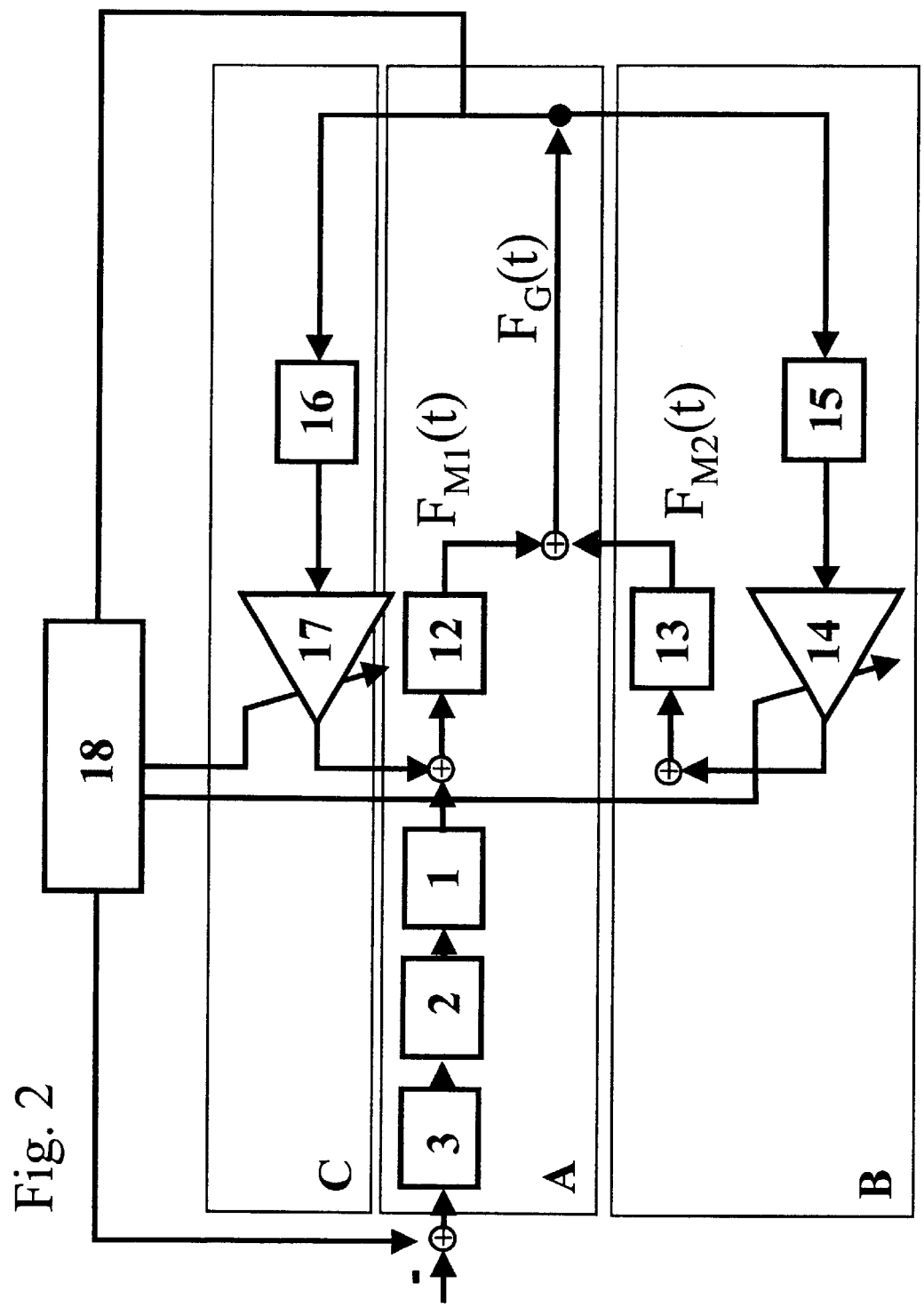
FIG. 2 shows a flow diagram of the stimulation according to the invention of a muscle and body reactions induced as a result.

The magnetic stimulation of a muscle as a result of a current pulse and its result on the stimulated muscle and the rest of the organism are illustrated on the basis of FIG. 2. The stimulation and its results can be subdivided into three systems A, B and C.

In the main system A, a pulse is emitted by the current pulse generator 3 (cf. also FIG. 1), via the power supply 2 concerned, to the coil 1 concerned for the stimulation of a muscle 12 of the limb, on the basis of the desired coordinates and the actual coordinates of the limb. This stimulation acts on the muscle 12 to be stimulated and thereby causes a movement of the limb. The new coordinates of the limbs after the movement are measured and passed to the current pulse generator 3 as new actual coordinates. The force exerted by the stimulated muscle 12, in the static case on a force-measuring instrument, for instance a pressure-dependent resistor, and in the dynamic case on an acceleration-measuring instrument, is denoted by $F_{M1}(t)$ Apart from this main system A, the movement of the limb is also influenced, however, by two secondary systems B and C. In the antagonistic secondary systems B, a movement of the antagonist 13, that is of the muscle opposing the stimulated muscle 12, is initiated by the movement of the stimulated muscle 12. When the stimulated muscle 12 contracts, the antagonist 13 expands and thereby retards or, more correctly, balances the movement of the simulated muscle 12. This takes place by an activation of the neuromuscular spindle 15 of the antagonist 13, this activation leading via the spinal cord 14, under the control of the central nervous system 18, by reflex action to a contraction of the antagonist 13. The force exerted by the antagonist 13 is denoted by $F_{M2}(t)$ The second secondary system C concerns the reflex coupling of the stimulated muscle 12 itself. By the movement of the stimulated muscle 12, the stimulation of this muscle 12 is directly influenced via its neuromuscular spindle 16 and via the spinal cord 17, under the control of the central nervous system 18. This coupling of the stimulated muscle 12 is contained in the force $F_{M1}(t)$. However, the coupling only contributes after a time delay to the contraction of the stimulated muscle 12, so that its influence on the variation of the force $F_{M1}(t)$ is not constant. While in healthy people these secondary systems are of minor significance, in patients with cerebral paralyses these secondary systems constitute very adverse factors for the force development of the stimulated muscle, due to the loss of inhibition of the reflexes.

The two secondary systems must be taken into account along with the main system in the stimulation of the muscle. This is because the movement of the limb follows the overall force $F_G(t)$, which represents the sum of the individual forces $F_{M1}(t)$ and $F_{M2}(t)$ To be able to control the effect of the stimulation, the result of a change in the stimulation on the movement of the limb must be determined. This requires the effects of the stimulation to be separated from the effects of the activation of the antagonist and the coupling. For this purpose, individual pulses are emitted by the current pulse generator at intervals of more than 5 seconds with increasing amplitude. This corresponds to weighted Dirac pulses. As a result, the system response of the main system of the muscle can be determined under the prescribed conditions.

FIG. 4 shows an example of the variation over time of the force $F_{M1}(t)$. This variation can be described by the exponential function $A*(\exp(-t/T1)-\exp(-t/T2))$. In the ideal case, this variation of force is equal to the overall force $F_G(t)$. The actual variation of the overall force represented in FIG. 3 differs, however, from the ideal variation by having a sharper drop after the maximum. This difference is relatively small in healthy people, but of great significance in patients with cerebral paralyses. This variation of the overall force $F_G(t)$ can be approximated by the exponential function described above. The variation of force $F_{M1}(t)$ is determined by this method. As can be seen in FIG. 2, the variation of the overall force $F_G(t)$ is obtained by a superimposing of the forces $F_{M1}(t)$ and $F_{M2}(t)$. It follows from this that the difference from the variation of the overall force $F_G(t)$ and the approximation by the exponential function $F_{M1}(t)$ represents the variation of the force of the second muscle $F_{M2}(t)$ on the basis of the antagonistic secondary system. The variation approximated by the exponential function is represented in FIG. 5. In this way, the influence of the antagonist on the simulated contraction can be determined, while the coupling of the stimulated muscle cannot be separated.

On the basis of the simulation system now determined, the starting values for the stimulation can be determined. Consequently, the response of the stimulated muscle when repetitive pulses are applied can be predicted and the effect of the stimulation can be assessed on this basis. During the stimulation, however, the response of the antagonist diminishes significantly. To achieve a slow, damped and monitored movement of the stimulated limb, the influence of the antagonist is therefore also determined and taken into account iteratively or adaptively in the closed loop during the stimulation.

Figure 6:
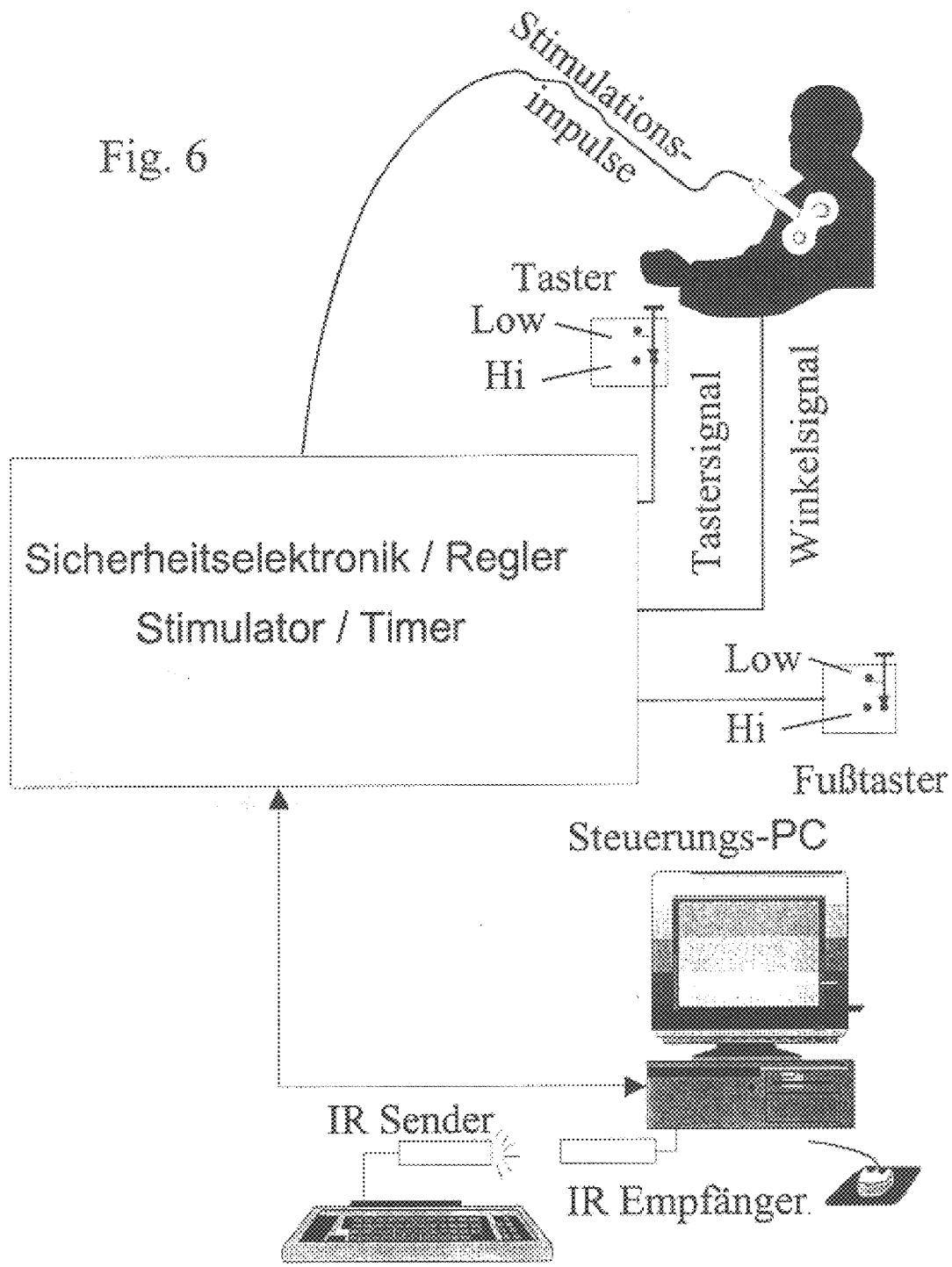
FIG. 6 shows a functional diagram of a device according to the invention with peripheral devices.

The device according to the invention and the method according to the invention preferably comprise a safety system. This safety system prevents the stimulation from taking place in an unintended way. FIG. 6 shows that this safety system has, inter alia, two pushbuttons. The patient keeps the first pushbutton pressed down during the stimulation. This makes it possible for the patient to end the stimulation as quickly as possible. The second pushbutton is a foot-operated pushbutton, with which the presence of a supervisor is ensured.

Either when the patient or the supervisor interrupts the pressing down of the pushbutton, no stimulation can take place in this time.

It can also be seen in FIG. 6 that the open-loop control unit of the stimulator preferably communicates with the stimulator via a non-conducting connection, in this case an infrared connection. Consequently, an electrical connection between the operator, the patient and the stimulation unit is prevented. This is particularly advantageous if an electrical connection between the patient and earth is to be prevented, which is advisable with regard to the currents possibly induced by the magnetic fields of the coils in the patient or the patient's direct surroundings, for instance the treatment chair. This is important in particular in the case of a defectively functioning coil.

In addition to these safety devices, a number of monitoring mechanisms also ensure stimulation of the patient as planned. For example, a timer function, which is in connection with the individual stimulators, prevents more than one stimulator ever being in operation at the same time. This can prevent the mutual effect of coils on one another, which could lead to unwanted transmissions of force to the patient and consequently to the patient being physically harmed.

What is claimed is:

1. Device for the stimulation of a body part, characterized in that it has at least the following elements:
    (a) at least one coil $S_i$ with at least one power supply for the generation of magnetic fields at an area of sensorimotor-terminal branches in order to induce direct, via stimulation, and indirect, via muscle contraction, sensorimotor input to produce a learning effect in the central nervous system, and
    (b) a device for the open-loop or closed-loop control of the at least one power supply for the coil $S_i$, which has at least the following element:
        a current pulse generator for the emission of current pulses $I(S_i)$ at pulse frequencies $f(I(S_i))$ and pulse durations $d(I(S_i))$ through the at least one power supply to the coil $S_i$ in such a way that the muscles of the body part are contracted or decontracted in a coordinated manner, so that a coordinated composite movement of the body part is obtained.

2. Device according to claim 1, characterized in that the device for the open-loop or closed-loop control of the at least one power supply for the coil $S_i$ has at least one sensor for sensing the position of the body part of controlling or regulating the at least one power supply for the coil $S_i$.

3. Device according to claim 1, characterized in that the device for the open-loop or closed-loop control of the at least one power supply for the coil $S_i$ includes a closed-loop control unit which responds to a signal which represents at least one state parameter for at least one muscle of the body part.

4. Device according to claim 3, characterized in that the signal is obtained from an electromyogram (EMG) measured at least one muscle of the body part.

5. Device according to claim 1, characterized in that the device for the open-loop or closed-loop control of the at least one power supply for the coil $S_i$ has at least one sensor for sensing forces acting on the body part for controlling or regulating that at least one power supply for the coil $S_i$.

6. Device according to claim 5, characterized in that at least one sensor is a pressure-dependent resistor.

7. Device according to claim 1, characterized in that the device for the open-loop or closed-loop control of the at least one power supply for the coil $S_i$ includes a learning algorithm, which influences the controlling or regulating of the at least one power supply for the coil $S_i$ on the basis of information on the movements of the body part carried out and on the state of the body part.

8. Device according to claim 1, characterized in that at least one pulse frequency $f(I(S_i))$ lies in the range from 15 Hz to 25 Hz to achieve maximum learning effect.

9. Device according to claim 1, characterized in that at least one current pulse $I(S_i)$ corresponds to a segment of a sinusoidal oscillation.

10. Device according to claim 9, characterized in that the segment of the sinusoidal oscillation extends from 0 to $2\pi$ in steps of $\pi/4$.

11. Method for the stimulation of a body part, characterized in that it has at least the following steps:
    (a) by means of at least one coil $S_i$ with at least one power supply, magnetic fields are generated at an area of sensorimotor-terminal branches in order to induce direct, via stimulation, and indirect, via muscle contraction, sensorimotor input to produce a learning effect in the central nervous system, and
    (b) by means of a device, the at least one power supply of the coil $S_i$ is controlled or regulated, the device having at least the following function:
        by means of a current pulse generator, current pulses $I(S_i)$ are emitted at pulse frequencies $f(I(S_i))$ and pulse durations $d(I(S_i))$ through the at least one power supply to the coil $S_i$ in such a way that the muscles of the body part are contracted or decontracted in a coordinated manner, so that a coordinated composite movement of the body part is obtained.

12. Method according to claim 11, characterized in that, with at least one sensor, the position of the body part is sensed for controlling or regulating the at least one power supply for the coil $S_i$, the sensor being part of the device for the open-loop or closed-loop control of the at least one power supply for the coil $S_i$.

13. Method according to claim 11, characterized in that the device for the open-loop or closed-loop control of the at least one power supply for the coil $S_i$ is equipped with a closed-loop control unit which responds to a signal which represents at least one state parameter for at least one muscle of the body part.

14. Method according to claim 13, characterized in that the signal is obtained from an electromyogram (EMG) measured at least one muscle of the body part.

15. Method according to claim 11, characterized in that the device for the open-loop or closed-loop control of the at least one power supply for the coil $S_i$ senses with at least one sensor the forces acting on the body part for controlling or regulating the at least one power supply for the coil $S_i$.

16. Method according to claim 15, characterized in that at least one sensor is a pressure-dependent resistor.

17. Method according to claim 11, characterized in that the device for the open-loop or closed-loop control of the at least one power supply for the coil $S_i$ influences with a learning algorithm the controlling or regulating of the at least one power supply for the coil $S_i$ on the basis of information on the movements of the body part carried out and on the state of the body part.

18. Method according to claim 11, characterized in that at least one pulse frequency $f(I(S_i))$ lies in the range from 15 Hz to 25 Hz to achieve maximum learning effect.

19. Method according to claim 11, characterized in that at least one current pulse $I(S_i)$ corresponds to a segment of a sinusoidal oscillation.

20. Method according to claim 19, characterized in that the segment of the sinusoidal oscillation extends from 0 to $2\pi$ in steps of $\pi/4$.

* * * * *